(12) United States Patent
Place

(10) Patent No.: US 6,221,379 B1
(45) Date of Patent: Apr. 24, 2001

(54) BUCCAL DRUG ADMINISTRATION IN FEMALE HORMONE REPLACEMENT THERAPY

(75) Inventor: Virgil A. Place, P.O. Box 44555-10 Ala Kahua, Kawaihae, HI (US) 96743

(73) Assignee: Virgil A. Place, Kawaihae, HI (US)

( * ) Notice: Subject to any disclaimer, the term of this patent is extended or adjusted under 35 U.S.C. 154(b) by 0 days.

(21) Appl. No.: 09/626,773

(22) Filed: Jul. 27, 2000

Related U.S. Application Data

(62) Division of application No. 09/237,713, filed on Jan. 26, 1999, now Pat. No. 6,117,446.

(51) Int. Cl.⁷ .................................................. A61F 13/02
(52) U.S. Cl. ........................................... 424/435; 424/435
(58) Field of Search ...................................... 424/434, 435

(56) References Cited

U.S. PATENT DOCUMENTS

| 4,507,323 | 3/1985 | Stern . |
|---|---|---|
| 4,521,421 | 6/1985 | Foreman . |
| 4,755,386 | 7/1988 | Hsiao et al. . |
| 4,764,378 | 8/1988 | Keith et al. . |
| 4,877,774 | 10/1989 | Pitha et al. . |
| 5,135,752 | 8/1992 | Snipes . |
| 5,190,967 | 3/1993 | Riley . |
| 5,346,701 | 9/1994 | Heiber et al. . |
| 5,516,523 | 5/1996 | Heiber et al. . |
| 5,543,154 | * 8/1996 | Rorok et al. . |
| 5,639,743 | 6/1997 | Kaswan et al. . |

* cited by examiner

Primary Examiner—Carlos A. Azpuru
(74) Attorney, Agent, or Firm—Dianne E. Reed; Reed & Associates

(57) ABSTRACT

A buccal dosage unit is provided for administering a combination of steroidal active agents to a female individual. The novel buccal drug delivery systems may be used in female hormone replacement therapy, in female contraception, to treat female sexual dysfunction, and to treat or prevent a variety of conditions and disorders which are responsive to the active agents discussed herein. The buccal dosage unit comprises a progestin, an estrogen and optionally an androgenic agent, as well as a polymeric carrier that bioerodes and provides for delivery of the active agents throughout a predetermined drug delivery period.

40 Claims, 2 Drawing Sheets

BUCCAL DRUG ADMINISTRATION IN FEMALE HORMONE REPLACEMENT THERAPY

CROSS-REFERENCE TO RELATED APPLICATIONS

This application is a divisional of U.S. patent application Ser. No. 09/237,713, now U.S. Pat. No. 6,117,446 filed Jan. 26, 1999.

TECHNICAL FIELD

This invention relates generally to pharmaceutical compositions and methods for administering pharmacologically active agents. More particularly, the invention relates to buccal drug delivery, and to a buccal dosage unit and method for administering a combination of steroidal active agents, e.g., for female hormone replacement therapy, female contraception, treatment of female sexual dysfunction, and the like.

BACKGROUND

Androgens are the hormones that cause most of the masculinizing changes that occur in males during puberty. *Harrison's Principles of Internal Medicine,* 12th Edition (New York, N.Y.: McGraw Hill, Inc., 1991). However, low levels of androgens are also present in normal females. Testosterone and other androgens are secreted by the ovary and the adrenal cortex. See, e.g., Goodman & Gilman's *The Pharmacological Basis of Therapeutics,* 9th Edition (New York, N.Y.: McGraw Hill, Inc., 1996). Dehydroepiandrosterone (DHEA) and androstenedione are also synthesized by both the adrenal gland and the ovary and can be converted to testosterone or estrogen in peripheral tissues. The daily rate of production of testosterone in women is on the order of 0.25 mg, about half of which is derived from the metabolic conversion of androstenedione to testosterone at extraglandular sites. The plasma concentration of testosterone in women alters with the menstrual cycle and ranges from 15 to 65 nanogramtdeciliter (ng/dl). As with estrogen, testosterone levels peak at the preovulatory and luteal phases of the cycle. At menopause, plasma androgen and estrogen levels are reduced but not completely absent in women. Alteration in the hormone profile is believed to be an underlying cause of menopausal symptoms in women, including vasomotor instability ("hot flash"), atrophy of the urogenital epithelium and skin, decreased size of the breasts and osteoporosis. See, e.g., *Harrison's Principles of Internal Medicine,* supra.

Alteration in normal hormonal levels can also cause sexual dysfunction. For example, estrogen deficiency, causing vaginal atrophy and dyspareunia, is a common cause of sexual dysfunction. Dyspareunia is thought to affect approximately 40% of women; it has been estimated that over 40 million female individuals will suffer dyspareunia at some time in their lives. On the order of twenty-five million women will experience dyspareunia in the peri- and post-menopausal periods (Kelly (1992) *Clinical Practice and Sexuality* 8(8):2; and Sato et al. (1992) *Clinical Practices in Sexuality* 8a(5):1.

Estrogen therapy is commonly used in the pharmacological treatment of altered hormone profiles or sexual dysfunction in women. Estrogen-based therapies are generally used to increase mucous production, provide vasodilator effects, and/or to increase the general health of the vagina. Nadelson et al., eds., *Treatment Interventions in Human Sexuality* (New York: Plenum Press, 1983). In such treatments, estrogen is administered orally, parenterally (e.g., by injection), or topically. With oral administration, as is true with the oral administration of many steroid hormones, estrogens tend to be inactivated; estradiol, for example, is converted to estriol and estrone and then conjugated to glucuronic acid or sulfate. Additionally, estrogens also impair hepatic secretory activity. This "first pass" effect may lead to an undesirable increase in the production of certain coagulation factors and other biologically important compounds by the liver. Parenterally administered estrogen avoids the aforementioned problems associated with oral administration. However, all estrogen-based therapies are known to increase the risk of endometrial hyperplasia and cancer, as well as the risk of breast cancer, in treated individuals.

Because of the increased risk of endometrial hyperplasia and endometrial cancer encountered with unopposed estrogen therapies, estrogen/progestin combinations have been employed. However, such therapies, as is well known, result in a number of side effects, including uterine bleeding and the continuation of menstrual periods. Accordingly, there remains a need in the art to provide safer and more effective treatments for administering active agents suitable for female hormone replacement therapy.

The present invention is directed in part to the aforementioned need in the art, and provides highly effective hormone replacement therapy for women in need of such treatment. The invention involves the use of a pharmaceutical composition in the form of a drug dosage unit to be applied to the buccal mucosa. In contrast to prior methods for effecting hormone replacement, the present invention avoids both gastrointestinal degradation of the drug and the "first pass" effect in the liver encountered with oral formulations, and enables the use of smaller doses of active agents (and thus avoids the side effects associated with conventional formulations). In addition, when an androgenic agent is included, as in the preferred embodiment herein, essentially complete hormone replacement is provided. That is, with respect to the latter point, estrogen/progestin therapies do not in fact provide "replacement" of the complete hormone profile of the premenopausal woman, because, as discussed above, androgens are also present in premenopausal women. In a preferred embodiment, then, the present invention calls for one or more androgenic agents to be administered along with a progestin and an estrogen.

The method and compositions of the invention may also be used to treat other conditions for which the disclosed hormone combination is useful. For example, the novel drug dosage units can be used to treat female sexual dysfunction, to effect female contraception, to improve vaginal muscle tone and tissue health, and to enhance vaginal lubrication.

Drug therapy for treating female sexual dysfunction has been described. For example, U.S. Pat. No. 4,507,323 to Stern describes the use of the anxiolytic m-chloro-α-t-butylamino-propiophenone in the treatment of sexual dysfunction in male and female individuals. Pharmaceutical compositions containing the agent are described, which are presented in discrete units, e.g., cachets, tablets, capsules, ampules and suppositories for oral or anal delivery of the agent. Additionally, U.S. Pat. No. 4,521,421 to Foreman describes the treatment of sexual dysfunction in male and female individuals using the stereoisomers of octahydropyrmidoquinoline agents, centrally acting dopamine agonists. U.S. Pat. No. 5,190,967 to Riley describes the treatment of sexual disorders in male and female individuals using heterocyclic benzodioxinopyrrole compounds, which, like the drugs described in the aforementioned patents, are centrally acting agents.

Drug therapy involving buccal administration of steroid hormones has also been described. For example, U.S. Pat. No. 4,755,386 to Hsiao et al. generally describes the buccal administration of various medicaments, including estrogens, progestins and androgens; combinations of the medicaments, however, are not contemplated. Furthermore, the buccal tablets of Hsiao et al., weighing on the order of 50 mg, contain adhesive, disintegrant and excipient in addition to the active agent, with the inactive ingredients representing up to about 90 wt. % of the formulation. U.S. Pat. No. 4,764,378 to Keith et al. describes rapidly disintegrating dosage forms utilizing a combination of high and low molecular weight polyethylene glycols; the dosage forms, which are preferably 50 mg to 100 mg tablets, may be administered orally or through the buccal mucosa. Similarly, U.S. Pat. No. 5,135,752 to Snipes et al. describes buccal delivery systems containing polyethylene glycols of varying molecular weights for the delivery of methyl testosterone or estradiol. In U.S. Pat. No. 4,877,774 to Pitha et al., crystalline complexes of steroid hormones and gamma-cyclodextrin are described for administration of steroids through mucosal tissue.

The buccal drug dosage units and methods of the present invention are, however, new and completely unsuggested by the art. Applicants' invention is premised on the discovery that steroidal agents, particularly an androgenic agent in combination with an estrogen and a progestin, can be buccally administered to provide for a highly effective method of female hormone replacement therapy. The buccal dosage units provided herein can also be used for other purposes, e.g., treatment of female sexual dysfunction, female contraception, improvement of vaginal muscle tone and tissue health, enhancement of vaginal lubrication, and the like.

SUMMARY OF THE INVENTION

Accordingly, it is a primary object of the invention to address the aforementioned need in the art by providing a drug dosage unit for buccally administering to a female individual a pharmaceutical composition comprising an estrogenic agent and a progestin, optionally in further combination with an androgenic agent.

It is another object of the invention to provide a method for administering a combination of steroidal agents to a female individual using the aforementioned drug dosage unit.

It is still another object of the invention to provide a method for facilitating delivery of a combination of steroidal active agents to an individual comprising affixing to the buccal mucosa of the individual a dosage unit as described herein and allowing the dosage unit to remain in place until erosion thereof is complete.

It is yet another object of the invention to provide female hormone replacement therapy by buccally administering a pharmaceutical composition as described herein to a woman in need of such therapy.

It is a further object of the invention to provide a method for effecting contraception in a fertile mammalian female by buccally administering a pharmaceutical composition as described herein.

It is still a further object of the invention to treat female sexual dysfunction by buccally administering a combination of active agents as described herein to a woman in need of such treatment.

It is an additional object of the invention to provide methods for improving vaginal muscle tone and tissue health and for enhancing vaginal lubrication, each of such methods involving buccal administration of a pharmaceutical composition as described herein to a woman in need of such treatment.

Additional objects, advantages and novel features of the invention will be set forth in part in the description which follows, and in part will become apparent to those skilled in the art upon examination of the following, or may be learned by practice of the invention.

Accordingly, in a first embodiment, a pharmaceutical composition is provided in the form of a simple, compact buccal dosage unit comprising therapeutically effective amounts of an androgenic agent, a progestin and an estrogen, or therapeutically effective amounts of an estrogen and a progestin, in a bioerodible polymeric carrier, wherein the carrier is such that it enables the dosage unit to adhere to the buccal mucosa. Following application to the buccal mucosa, gradual and complete erosion of the unit occurs over a predetermined time period, thus providing drug delivery throughout that time period. In a preferred embodiment, the dosage unit contains only the active agents to be administered and the polymeric carrier. However, other components, particularly a lubricant, may be incorporated to facilitate manufacture of the unit or if otherwise found to be necessary or desirable. The buccal dosage units are typically far smaller than conventional buccal delivery systems—the present tablets are on the order of 5–20 mg, typically 10–15 mg—and do not require a plurality of excipients, disintegrants, adhesives, or the like, nor are fragrances or permeation enhancers necessary. Accordingly, the novel dosage units are more comfortable than conventional systems because of their compact size. The novel units are also highly effective in providing therapeutically effective levels of steroidal agents. While the dosage units are designed to erode and thus deliver the active agents over a predetermined time period that is generally in the range of about 8 hours to about 24 hours, 12-hour dosage units are preferred, such that the individual receiving drug therapy can conveniently use two dosage units in a 12-hour period, enabling two "breaks" for dental hygiene or the like during the day. In this regard, the dosage units can be applied to an area of a subject's buccal mucosa such that the subject can eat and/or drink with the unit in place.

In another aspect of the invention, a method is provided for administering a combination of steroidal agents to a female individual using the aforementioned buccal dosage units, to treat any disorder, condition, disease or dysfunction for which the combination of an estrogen, a progestin, and, optionally, an androgenic agent, be indicated. The combination of active agents may be administered, for example, to provide female hormone replacement therapy, to effect female contraception, to treat female sexual dysfunction, to improve vaginal muscle tone and tissue health, to enhance vaginal lubrication, and the like. The active agents are administered through the buocal mucosa by affixing a dosage unit as provided herein to the buccal mucosa of the individual undergoing treatment, and allowing the dosage unit to remain in place until erosion thereof and thus drug delivery is complete. Preferably, the dosage unit is affixed to the upper gum area in a region defined as extending from the first bicuspid on the left to the first bicuspid on the right; an alternative preferred location for the dosage unit is the inner lip area opposing the aforementioned gum area.

A further embodiment of the invention relates to a kit for assisting an individual in buccal drug administration. Generally, the kit includes the following components: a buccal dosage unit comprising a combination of steroidal active agents in a bioerodible polymeric carrier; a container housing the dosage unit prior to use; and written instructions for carrying out administration of the active agents for the intended therapeutic purpose.

DETAILED DESCRIPTION OF THE INVENTION

Figure 1:
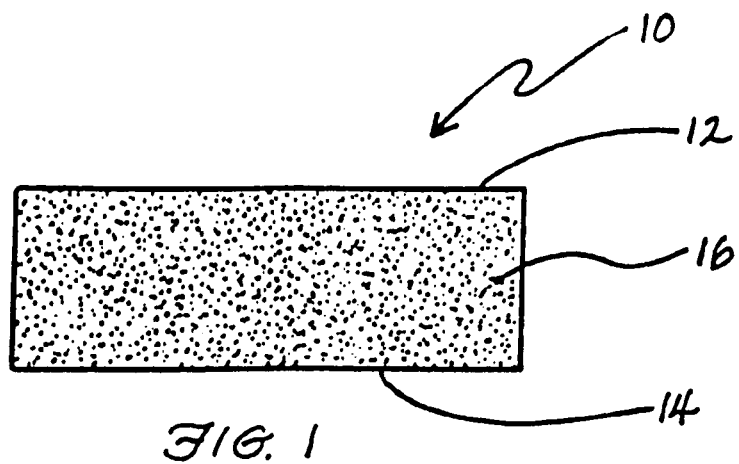
FIG. 1 schematically illustrates one embodiment of a buccal dosage unit according to the invention.

Before describing the present invention in detail, it is to be understood that this invention is not limited to specific active agents or carriers as such may vary. It is also to be understood that the terminology used herein is for the purpose of describing particular embodiments only, and is not intended to be limiting.

It must be noted that, as used in this specification and the appended claims, the singular forms "a", "an" and "the" include plural referents unless the context clearly dictates otherwise. Thus, for example, reference to "an estrogen" or "an estrogenic agent" includes a mixture of two or more such active agents, reference to "a buccal permeation enhancer" includes mixtures of two or more enhancers, reference to "a carrier" or "an excipient" includes a combination of two or more such materials, and the like.

In describing and claiming the present invention, the following terminology will be used in accordance with the definitions set out below.

The terms "drug" or "pharmacologically active agent" or "active agent" are used interchangeably herein to refer to a compound or composition of matter which, when administered to an organism (human or animal) induces a desired pharmacologic and/or physiologic effect by local and/or systemic action. The active agents herein are steroid hormones, including androgenic agents, e.g., testosterone and derivatives, analogs, esters and salts thereof, progestins (also referred to herein and in the art as "progestogens"), e.g., progesterone and the like, and estrogens, e.g., ethynyl estradiol and the like.

By "buccal" drug delivery is meant delivery of a drug by passage of a drug through the buccal mucosa into the bloodstream. Preferably, buccal drug delivery is effected herein by placing the buccal dosage unit on the upper gum or opposing inner lip area of the individual undergoing drug therapy.

"Penetration enhancement" or "permeation enhancement" as used herein relates to an increase in the permeability of the buccal mucosal tissue to a pharmacologically active agent, i.e., so that the rate at which the drug permeates through the mucosal tissue is increased.

"Excipients" or "vehicles" as used herein refer to any excipients or vehicles suitable for buccal drug administration, and include any such materials known in the art, e.g., any liquid, gel, solvent, liquid diluent, solubilizer, or the like, which is nontoxic and does not interact with other components of the composition in a deleterious manner.

By an "effective" or "therapeutically effective" amount of a drug or pharmacologically active agent is meant a nontoxic but sufficient amount of the drug or agent to provide the desired effect. An "effective" amount of a permeation enhancer as used herein means an amount that will provide the desired increase in the rate at which an active agent passes through the tissue of the buccal mucosa.

"Compact" as used herein refers to a buccal dosage unit that is preferably no larger than about 5 mm in diameter and 2 mm in height, so that the unit occupies at most about 40 $mm^3$, typically weighs less than about 40 mg (preferably 5 to 20 mg, more preferably 10 to 15 mg), and has a contact surface area of no more than approximately 20 $mm^3$.

The terms "erodible" and "bioerodible" as used herein refer to a compound or composition that hydrolyzes upon contact with the buccal mucosa.

By "female sexual dysfunction" is meant any and all types of sexual dysfunction in human females, including, but not limited to, excitement stage dysfunctions such as touch sensation impairment, loss of clitoral sensation, and vaginal dryness and concomitant dyspareunia. Other types of female sexual dysfunction are discussed in detail by Kaplan, *The Evaluation of Sexual Disorders: Psychological and Medical Aspects* (New York, N.Y.: Brunner-Mazel, 1983), and by Kolodny et al., *Textbook of Sexual Medicine* (Boston, Mass.: Little, Brown & Co., 1979). Reference may be had to those texts for information not explicitly discussed herein.

The terms "treating" and "treatment" as used herein refer to reduction in severity and/or frequency of symptoms, elimination of symptoms and/or underlying cause, prevention of the occurrence of symptoms and/or their underlying cause, and improvement or remediaton of damage. Thus, for example, the present method of "treating" female sexual dysfunction, as the term "treating" is used herein, encompasses both prevention of female sexual dysfunction and treatment of the dysfunction in a clinically symptomatic individual.

In one embodiment, then, a pharmaceutical composition is provided in the form of a buccal dosage unit for the administration of a combination of steroidal agents. The dosage unit comprises (a) therapeutically effective amounts of an androgenic agent, a progestin and an estrogen, or of a progestin and an estrogen, and (b) a bioerodible polymeric carrier as will be described in detail below. The dosage unit is fabricated so as to erode gradually over a predetermined time period, wherein drug delivery is provided essentially throughout. The time period is typically in the range of 8 hours to 24 hours; that is, for an 8-hour unit, erosion will occur throughout an 8-hour period and be substantially complete at the 8-hour point, while for a 24-hour unit, erosion will occur throughout a 24-hour period and be substantially complete at the 24-hour point. The buccal dosage unit may further comprise a lubricant to facilitate manufacture, e.g., magnesium stearate or the like. Additional components that may be included in the buccal dosage unit, but are neither required nor preferred, are flavorings, permeation enhancers, diluents, binders, and the like. As a buccal drug delivery system, the novel dosage unit avoids the disadvantages encountered with oral drug administration, e.g., degradation of the agents by fluids present in the gastrointestinal tract and/or first-pass inactivation in the liver. In addition, because of its compact size, the unit is not associated with the discomfort encountered with larger, conventional buccal drug delivery systems. Also, the units are convenient in that the wearer need change the unit only once or twice daily, i.e., with 24-hour or 12-hour systems, respectively; a 12-hour unit to be applied once in the morning and once in the evening is optimal. Finally, because of the compositional simplicity of the unit—in a preferred embodiment, the unit contains only the active agents and the polymeric carrier—manufacture of the dosage form is straightforward and economical.

The buccal dosage units of the invention are useful in providing effective female hormone replacement therapy, in that the occurrence of symptoms or conditions resulting from altered hormone levels is mitigated or substantially prevented. The invention is thus useful to treat women for whom ovarian steroid production has been altered, either because of menopause, surgical or radiation treatment, ovarian ablation, or premature ovarian failure. As noted elsewhere herein, the invention is also useful to treat female sexual dysfunction, to effect female contraception, to improve vaginal muscle tone and tissue health, and for enhancing vaginal lubrication. Each buccal dosage unit will contain an androgenic agent, a progestin, and an estrogen, or a progestin and an estrogen.

Suitable androgenic agents that may be used in the formulations of the present invention include, but are not limited to: the naturally occurring androgens and derivatives thereof including androsterone, androsterone acetate, androsterone propionate, androsterone benzoate, androstenediol, androstenediol-3-acetate, androstenediol-17-acetate, androstenediol-3,17-diacetate, androstenediol-17-benzoate, androstenediol-3-acetate-17-benzoate, androstenedione, dehydroepiandrosterone (DHEA; also termed "prasterone"), sodium dehydroepiandrosterone sulfate, 4-dihydrotestosterone (DHT; also termed "stanolone"), 5α-dihydrotestosterone, dromostanolone, dromostanolone propionate, ethylestrenol, nandrolone phenpropionate, nandrolone decanoate, nandrolone furylpropionate, nandrolone cyclohexanepropionate, nandrolone benzoate, nandrolone cyclohexanecarboxylate, oxandrolone, stanozolol and testosterone; pharmaceutically acceptable esters of testosterone and 4-dihydrotestosterone, typically esters formed from the hydroxyl group present at the C-17 position, including, but not limited to, the enanthate, propionate, cypionate, phenylacetate, acetate, isobutyrate, buciclate, heptanoate, decanoate, undecanoate, caprate and isocaprate esters; and pharmaceutically acceptable derivatives of testosterone such as methyl testosterone, testolactone, oxymetholone and fluoxymesterone. Testosterone and testosterone esters, such as testosterone enanthate, testosterone propionate and testosterone cypionate, are particularly preferred androgenic agents for use in conjunction with the present invention. The aforementioned testosterone esters are commercially available or may be readily prepared using techniques known to those skilled in the art or described in the pertinent literature. (Generally, the 17-hydroxyl group of the testosterone molecule is caused to react with a suitable organic acid under esterifying conditions, such conditions typically involving the use of a strong acid such as sulfuric acid, hydrochloric acid, or the like, and a temperature sufficient to allow the reaction to proceed at reflux.)

Suitable estrogens that may be administered using the dosage units of the invention include synthetic and natural estrogens such as: estradiol (i.e., 1,3,5-estratriene-3,17β-diol, or "β-estradiol") and its esters, including estradiol benzoate, valerate, cypionate, heptanoate, decanoate, acetate and diacetate; 17α-estradiol; ethynylestradiol (i.e., 17α-ethynylestradiol) and esters and ethers thereof including ethynylestradiol 3-acetate and ethynylestradiol 3-benzoate; estriol and estriol succinate; polyestrol phosphate; estrone and its esters and derivatives, including estrone acetate, estrone sulfate, and piperazine estrone sulfate; quinestrol; mestranol; and conjugated equine estrogens. Estradiol and ethynylestradiol are particularly preferred synthetic estrogenic agents for use in conjunction with the present invention.

Suitable progestins for use in the buccal drug delivery units of the invention include, but are not limited to, acetoxypregnenolone, allylestrenol, anagestone acetate, chlormadinone acetate, cyproterone, cyproterone acetate, desogestrel, dihydrogesterone, dimethisterone, ethisterone (17α-ethynyltestosterone), ethynodiol diacetate, flurogestone acetate, gestadene, hydroxyprogesterone, hydroxyprogesterone acetate, hydroxyprogesterone caproate, hydroxymethylprogesterone, hydroxymethylprogesterone acetate, 3-ketodesogestrel, levonorgestrel, lynestrenol, medrogestone, medroxyprogesterone acetate, megestrol, megestrol acetate, melengestrol acetate, norethindrone, norethindrone acetate, norethisterone, norethisterone acetate, norethynodrel, norgestimate, norgestrel, norgestrienone, normethisterone, and progesterone. Progesterone, cyproterone acetate, norethindrone, norethindrone acetate and levonorgestrel are preferred progestins.

The aforementioned steroidal agents are selected from the group consisting of naturally occurring steroids, synthetic steroids, and derivatives thereof. The active agents may be incorporated into the present dosage units and thus administered in the form of a pharmaceutically acceptable derivative, analog, ester or salt, or the agents may be modified by appending one or more appropriate functionalities to enhance selected biological properties such as penetration through the mucosal tissue. In general, when the buccal dosage units are used to administer androgenic agents, esters are preferred relative to salts or other derivatives. Preparation of esters involves functionalization of hydroxyl and/or carboxyl groups that may be present, as will be appreciated by those skilled in the arts of pharmaceutical chemistry and drug delivery. Esters can be reconverted to the free acids, if desired, by using conventional hydrogenolysis or hydrolysis procedures.

To administer any one of the active agents in salt form, suitable pharmaceutically acceptable salts can be prepared using standard procedures known to those skilled in the art of synthetic organic chemistry and described, for example, by J. March, *Advanced Organic Chemistry: Reactions, Mechanisms and Structure,* 4th Ed. (New York: Wiley-Interscience, 1992). Acid addition salts are prepared from an active agent in the free base form (e.g., compounds having a neutral —$NH_2$ group) using conventional means, involving reaction with a suitable acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Preparation of basic salts of acid moieties which may be present (e.g., carboxylic acid groups) are prepared in a similar manner using a pharmaceutically acceptable base such as sodium hydroxide, potassium hydroxide, ammonium hydroxide, calcium hydroxide, magnesium hydroxide, trimethylamine, or the like.

For those active agents that are chiral in nature and can thus be in enantiomerically pure form or in a racemic mixture, the drug may be incorporated into the present dosage units either as the racemate or in enantiomerically pure form.

The quantity of each active agent in the buccal dosage unit will depend on a number of factors, including the potency of each agent and the intended dosage, which, in turn, is dependent on the particular individual undergoing treatment, the specific indication, and the like. Generally, when present the androgenic agent represents approximately 5 wt. % to 20 wt. %, preferably 10 wt. % to 20 wt. %, of the buccal dosage unit, the progestin represents approximately 5 wt. % to 60 wt. %, preferably 30 wt. % to 60 wt. %, of the dosage unit, and the estrogen represents approximately 1 wt. % to 5 wt. %, preferably 2 wt. % to 5 wt. %, of the buccal dosage unit. The remainder of the buccal dosage unit comprises the bioerodible polymeric carrier, as will be described in detail below, and any excipients that may be desired, e.g., binders, disintegrants, lubricants, diluents, flavorings, colorings, and the like, and/or additional active agents.

Ideally, the carrier comprises a polymer having sufficient tack to ensure that the dosage unit adheres to the buccal mucosa for the necessary time period, i.e., the time period during which the combination of active agents is to be delivered to the buccal mucosa. Additionally,. the polymeric carrier is gradually "bioerodible," i.e., the polymer hydrolyzes at a predetermined rate upon contact with moisture. The polymeric carrier is preferably sticky when moist, but not when dry, for convenience in handling. Generally, it is preferred that the weight average molecular weight ($M_w$) of the polymer be in the range of approximately 4,000 to 1,000,000, more preferably in the range of approximately 100,000 to 1,000,000. One of skill in the art will appreciate that the higher the molecular weight of the polymer, the slower the erosion time.

Any polymeric carriers can be used that are pharmaceutically acceptable, provide both a suitable degree of adhesion and the desired drug release profile, and are compatible with the agents to be administered and any other components that may be present in the buccal dosage unit. Generally, the polymeric carriers comprise hydrophilic (water-soluble and water-swellable) polymers that adhere to the wet surface of the buccal mucosa. Examples of polymeric carriers useful herein include acrylic acid polymers and copolymers, e.g., those known as "carbomers" (Carbopol®, which may be obtained from B. F. Goodrich, is one such polymer). Other suitable polymers include, but are not limited to: hydrolyzed polyvinylalcohol; polyethylene oxides (e.g., Sentry Polyox® water soluble resins, available-from Union Carbide); polyacrylates (e.g., Gantrez®, which may be obtained from GAF); vinyl polymers and copolymers; polyvinylpyrrolidone; dextran; guar gum; pectins; starches; and cellulosic polymers such as hydroxypropyl methylcellulose (e.g., Methocel®, which may be obtained from the Dow Chemical Company), hydroxypropyl cellulose (e.g., Klucel®, which may also be obtained from Dow), hydroxypropyl cellulose ethers (see, e.g., U.S. Pat. No. 4,704,285 to Alderman), hydroxyethyl cellulose, sodium carboxymethyl cellulose, methyl cellulose, ethyl cellulose, cellulose acetate phthalate, cellulose acetate butyrate, and the like. The carrier may also comprise two or more suitable polymers in combination, for example, a carbomer combined in an approximately 1:5 to 5:1 ratio, by weight, with a polyethylene oxide.

It is preferred that the present dosage unit contain only the active agents and the polymeric carrier. However, it may be desirable in some cases to include one or more additional components. For example, a lubricant may be included to facilitate the process of manufacturing the dosage units; lubricants may also optimize erosion rate and drug flux. If a lubricant is present, it will represent on the order of 0.01 wt. % to about 2 wt. %, preferably about 0.01 wt. % to 0.5 wt, %, of the dosage unit. Suitable lubricants include, but are not limited to, magnesium stearate, calcium stearate, stearic acid, sodium stearylfamarate, talc, hydrogenated vegetable oils and polyethylene glycol. As will be appreciated by those skilled in the art, however, modulating the particle size of the components in the dosage unit and/or the density of the unit can provide a similar effect—i.e., improved manufacturability and optimization of erosion rate and drug flux—without addition of a lubricant.

Other components may also be incorporated into the buccal dosage unit; however, it must be emphasized that such components are neither required nor preferred. Such additional optional components include, for example, one or more disintegrants, diluents, binders, enhancers, or the like. Examples of disintegrants that may be used include, but are not limited to, cross-linked polyvinylpyrrolidones, such as crospovidone (e.g., Polyplasdone® XL, which may be obtained from GAF), cross-linked carboxylic methylceiluloses, such as croscarmelose (e.g., Ac-di-sol®, which may be obtained from FMC), alginic acid, and sodium carboxymethyl starches (e.g., Explotab®, which may be obtained from Edward Medell Co., Inc.), agar bentonite and alginic acid. Suitable diluents are those which are generally useful in pharmaceutical formulations prepared using compression techniques, e.g., dicalcium phosphate dihydrate (e.g., Di-Tab®, which may be obtained from Stauffer), sugars that have been processed by cocrystallization with dextrin (e.g., co-crystallized sucrose and dextrin such as Di-Pak®, which may be obtained from Amstar), lactone, calcium phosphate, cellulose, kaolin, mannitol, sodium chloride, dry starch, powdered sugar and the like. Binders, if used, are those that enhance adhesion. Examples of such binders include, but are not limited to, starch, gelatin and sugars such as sucrose, dextrose, molasses, and lactose. Permeation enhancers may also be present in the novel dosage units in order to increase the rate at which the active agents pass through the buccal mucosa. Examples of permeation enhancers include, but are not limited to, dimethylsulfoxide ("DMSO"), dimethyl formamide ("DMF"), N,N-dimethylacetamide ("DMA"), decylmethylsulfoxide ("$C_{10}MSO$"), polyethylene glycol monolaurate ("PEGML"), glycerol monolaurate, lecithin, the 1-substituted azacycloheptan-2-ones, particularly 1-n-dodecylcyclazacycloheptan-2-one (available under the trademark Azone® from Nelson Research & Development Co., Irvine, Calif.), lower alkanols (e.g., ethanol), SEPA® (available from Macrochem Co., Lexington, Mass.), cholic acid, taurocholic acid, bile salt type enhancers, and surfactants such as Tergitol®, Nonoxynol-9® and TWEEN-80®. Preferred dosage units of the invention, however, do not contain permeation enhancers.

Flavorings are not typically needed in the present drug dosage units, as the active agents do not, in general, have any taste. If for some reason a flavoring is desired, any suitable flavoring may be used, e.g., mannitol, lactose or artificial sweeteners such as aspartame. Coloring agents may be added, although again, such agents are not required. Examples of coloring agents include any of the water soluble FD&C dyes, mixtures of the same, or their corresponding lakes.

In addition, if desired, the present dosage units may be formulated with one or more preservatives or bacteriostatic agents, e.g., methyl hydroxybenzoate, propyl hydroxybenzoate, chlorocresol, benzalkonium chloride, or the like.

Also, one or more additional types of drugs, i.e., pharmacologically active agents other than androgenic agents, progestins and estrogens, may be incorporated into the present dosage units.

In general, the dosage unit of the invention is compositionally a substantially homogeneous, substantially uniform formulation. By "substantially uniform" is meant that the dosage unit is not coated, does not have a backing, and does not contain a plurality of layers or other types of discrete segments. Rather, the substance of the dosage unit is similar throughout, so that the unit is essentially "monolithic" in nature.

In another embodiment of the invention, a method is provided for administering a combination of steroidal agents using the buccal dosage units described hereinabove, containing an androgenic agent, a progestin, and an estrogen, or a progestin and an estrogen. The method generally comprises buccally administering the combination of active agents by affixing the dosage unit of the invention to the buccal mucosa of the individual and allowing the dosage unit to remain in place until erosion thereof—and thus drug delivery—is complete. Administration of a combination of steroidal active agents in this way is useful in a variety of contexts, as will be readily appreciated by those skilled in the art. For example, the buccal administration of the aforementioned combinations of steroidal agents may be used in female hormone replacement therapy, so that the symptoms or conditions resulting from altered hormone levels is mitigated or substantially prevented. As alluded to above, the method is also useful in other contexts, e.g., treatment of female sexual dysfunction, effecting female contraception, improving vaginal muscle tone and tissue health, and enhancing vaginal lubrication. The buccal dosage units and present method of administering active agents therewith are in addition useful to treat other conditions and disorders that are responsive to buccal administration of the combination of active agents disclosed herein. For example, the invention is useful to treat the symptoms of premenstrual stress, osteoporosis, dry eye, the wasting syndrome accompanying AIDS (e.g., unintentional weight loss, decrease in lean body mass) and some autoimmune diseases, including but not limited to Sjogren's syndrome (see, e.g., U.S. Pat. No. 5,639,743).

For female hormone replacement therapy, the woman undergoing treatment will generally be of childbearing age or older, in whom ovarian estrogen, progesterone and androgen production has been interrupted either because of natural menopause, surgical procedures, radiation, chemical ovarian ablation or extirpation, or premature ovarian failure. Preferred dosage units for hormone replacement therapy are capable of delivering about 0.1 to about 2.5 mg of the selected androgenic agent, preferably testosterone or a testosterone ester, e.g., testosterone enanthate, cypionate or propionate, about 300 to 5000 $\mu$g progestin, e.g., norethindrone, norethindrone acetate or the like, and about 50 to 500 $\mu$g estrogen, e.g., estradiol, ethynyl estradiol or the like, over a period of about 24 hours. However, it will be appreciated by those skilled in the art that the desired dose of each individual active agent will depend on the specific active agent as well as on other factors; the minimum effective dose of each active agent is of course preferred. Also, as noted above, in general, the androgenic agent when present represents 5 wt. % to 20 wt. %, preferably 10 wt. % to 20 wt. %, of the buccal dosage unit, the progestin represents approximately 5 wt. % to 60 wt. %, preferably 30 wt. % to 60 wt. %, of the dosage unit, and the estrogen represents approximately 1 wt. % to 5 wt. %, preferably 2 wt. % to 5 wt. %, of the buccal dosage unit.

For hormone replacement therapy, and for the other indications described herein including treatment of female sexual dysfunction, the buccal dosage units are preferably used consecutively so that administration of the active agents is substantially continuous. Buccal drug administration according to the invention provides highly effective female hormone replacement therapy. That is, the incidence and severity of hot flashes and night sweats are reduced, postmenopausal loss of calcium from bone is minimized, the risk of death from ischemic heart disease is reduced, and the vascularity and health of the vaginal mucosa and urinary tract are improved. At the same time, the side effects normally expected and encountered with conventional hormone replacement are minimized or eliminated.

In treating female sexual dysfunction, and for the other indications described herein, the dosage and administration period will, again, vary depending on the individual and the severity of sexual dysfunction or other condition; however, in general, the preferred dosage and treatment regimen is as described above for hormone replacement therapy.

The buccal dosage units may be in the form of tablets made by either conventional compression or molding methods. See, e.g., *Remington's Pharmaceutical Sciences*, 18th edition (Easton, Pa.: Mack Publishing Co., 1990). Preferably, the dosage units are prepared by mixing the components together and compressing the mixture into tablet form. As will be appreciated by those skilled in the art, the erosion rate of the dosage unit, and thus the rate of drug delivery, is controlled by three factors: the pressure used to make the tablets, and thus the tablets' density; the carrier selected, as alluded to above; and the carrier-to-drug ratio. Pressure, carrier and carrier-to-drug ratio may thus be varied to obtain shorter acting or longer-lived dosage units.

Figure 2:
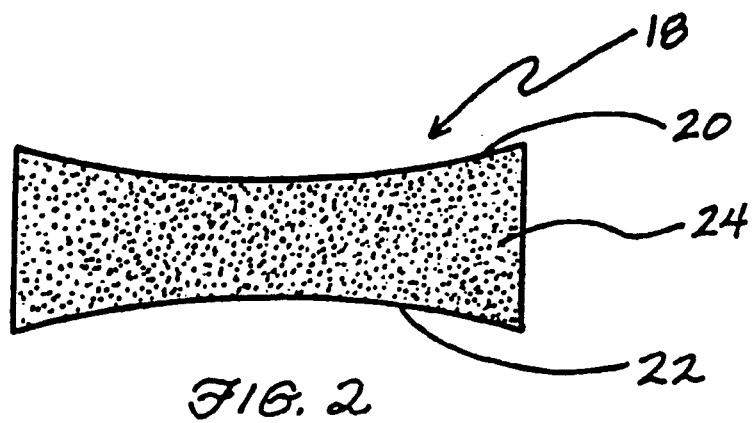
FIG. 2 schematically illustrates an alternative and preferred embodiment of a buccal dosage unit according to the invention.
Figure 3:
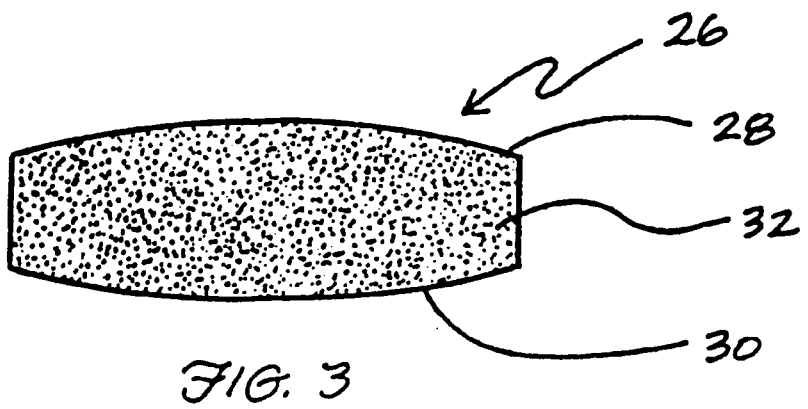
FIG. 3 schematically illustrates a second alternative embodiment of a buccal dosage unit according to the invention.

The dosage units may have any of the conventional shapes, for example, lozenges, disks, wafers, tablets or the like. One possible configuration is a conventional tablet shape as shown in FIG. 1, with the dosage unit indicated generally at 10, the pharmaceutical composition per se shown at 12, and the dosage unit's two parallel substantially planar surfaces shown at 14 and 16; either surface can be used to affix the unit to the buccal mucosa. A more preferred configuration is shown in FIG. 2, wherein the dosage unit is shown generally at 18 with the composition at 20, and the two opposing concave surfaces at 22 and 24; the opposing concave surfaces allow for a suction effect and improve adhesion of the unit to the mucosal tissue. It will be appreciated, of course, that only one of the two surfaces need be concave to achieve the desired suction effect. A less preferred configuration is shown in FIG. 3, wherein the dosage unit shown generally at 26, containing pharmaceutical composition 28, has opposing convex surfaces 30 and 32.

The dosage unit should have dimensions which fit conveniently into the buccal cavity, and, as emphasized elsewhere herein, is preferably quite compact. By way of example, suitable dimensions for the dosage unit are 2 mm to about 5 mm in diameter, preferably not exceeding about 5 mm in diameter, and about 0.3 to about 2 mm in thickness, preferably about 0.5 to 1.5 mm in thickness, most preferably about 0.5 to 1.1 mm in thickness. The total weight of the dosage unit may be from about 5 mg to about 20 mg, preferably 10 mg to about 15 mg.

The buccal dosage units may also be generated by a molding process. Preferably, the final unit should have a melting point which is high enough to prevent fusion of packaged dosage units during shipping and storage, yet low enough to permit mixing of pharmaceutical ingredients without significant decomposition of the active agents when being incorporated into the molten carrier.

Figure 4:
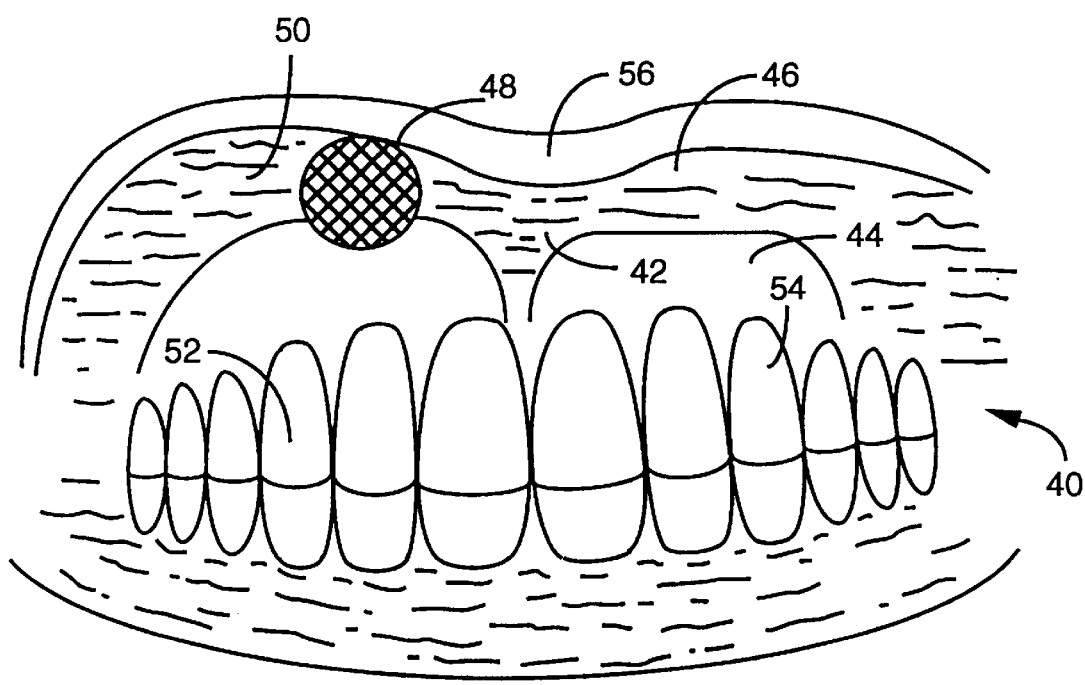
FIG. 4 illustrates the placement of the buccal dosage unit in the preferred location in the oral cavity.

The preferred position for placement of the dosage unit in the buccal cavity, as illustrated in FIG. 4, is in the oral vestibule, generally indicated at 40, on the anterior surface 42 of the gum, between the marginal gingiva 44 and the reflexion of the mucosa from the lips to the gums 46, i.e., the dosage unit 48 is preferably attached to the alveolar mucosa 50, between the two bicuspids 52 and 54 and slightly to one side of the medial plane defined thereby. Such positioning places the dosage unit in contact with the mucosa on the internal surface of the lips 56 as well as the alveolar mucosa 50. Such placement provides advantages for optimal drug delivery. For example, when so positioned, the dosage unit is out of the salivary flow path and is less likely to detach from the gum when the subject eats or drinks. Being out of the salivary flow path allows optimal direct transmucosal delivery of the active agents, any saliva that contacts the unit resulting not in dissolution of the active agents but, primarily, in softening the carrier. In addition, positioning the dosage unit as described minimizes mobility of the active agents in the mouth. Furthermore, the dosage unit will be in contact with both the alveolar mucosa and the internal mucosal surface of the lips, resulting in hydrolysis of the carrier, and thus absorption of the active agents through mucosa, on both sides of the tablet.

The invention also encompasses a kit for patients to carry out the aforementioned methods. The kit contains the drug to be administered in a buccal dosage unit (e.g., as shown in FIGS. 1, 2 or 3), a sealed container housing the dosage unit prior to use, and written instructions for drug administration.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

EXAMPLE 1

Buccal dosage units weighing approximately 10 mg each and containing testosterone, estradiol and progesterone as the active agents were prepared using a tablet direct press, as follows.

Tablet Composition

| % BY WEIGHT | WEIGHT (mg) | COMPONENT |
| --- | --- | --- |
| 15% | 1.5 | Testosterone (USP, micronized, Pharmacia Upjohn) |
| 3% | 0.3 | Estradiol (USP, micronized, Pharmacia Upjohn) |
| 47% | 4.7 | Progesterone (USP, micronized, Pharmacia Upjohn) |
| 24.8% | 2.48 | Polyethylene oxide (Polyox ® WSR-303, Union Carbide) |
| 10% | 1.0 | Carbomer (Carbopol ® NF) |
| 0.2% | 0.02 | Magnesium Stearate |
| 100% | 10.00 mg | |

All components (i.e., testosterone, estradiol, polyethylene oxide, carbomer, and magnesium stearate, as set forth in the above table) were thoroughly mixed prior to tablet formation using aqueous fluid bed granulation to provide a homogeneous mixture of active agents and excipients. The individual dosage units were then made by applying 10 mg of the mixture into the punch die of the tablet press, and compressing the mixed components using a pressure in the range of approximately 500 to 2000 psi. Tablets having a diameter of approximately 4 mm and a height of 1 mm were prepared. The tablets were removed from the punch die and the weight and dimensions of the tablets were measured.

EXAMPLE 2

Buccal dosage units weighing approximately 10 mg each and containing testosterone, ethynyl estradiol and progesterone as the active agents, were prepared using a tablet direct press, as follows.

Tablet Composition

| % BY WEIGHT | WEIGHT (mg) | COMPONENT |
| --- | --- | --- |
| 15% | 1.5 | Testosterone (USP, micronized, Pharmacia Upjohn) |
| 3% | 0.3 | Ethynyl estradiol (USP, micronized, Pharmacia Upjohn) |
| 47% | 4.7 | Progesterone (USP, micronized, Pharmacia Upjohn) |
| 24.8% | 2.48 | Polyethylene oxide (Polyox ® WSR-303, Union Carbide) |
| 10% | 1.0 | Carbomer (Carbopol ® NF) |
| 0.2% | 0.02 | Magnesium Stearate |
| 100% | 10.00 mg | |

All components (i.e., testosterone, ethynyl estradiol, polyethylene oxide, carbomer, and magnesium stearate, as set forth in the above table) were thoroughly mixed prior to tablet formation using aqueous fluid bed granulation to provide a homogeneous mixture of active agents and excipients. As in Example 1, the individual dosage units were then made by applying approximately 10 mg of the mixture into the punch die of the tablet press, and compressing the mixed components using a pressure in the range of approximately 500 to 2000 psi. Tablets having a diameter of approximately 4 mm and a height of 1 mm were prepared. The tablets were removed from the punch die and the weight and dimensions of the tablets were measured.

EXAMPLE 3

Female patients in need of hormone replacement may be administered the buccal dosage unit described in Example 1 or Example 2 every 24-hour period. Plasma levels of androgen, progestin and estrogen are measured using conventional methodology, both prior to treatment and at intervals after the start of treatment. The change in steroid hormone levels prior to and following treatment may be used to assess the efficacy of the hormone supplement. Based on these measurements, a determination is made as to whether or not hormone levels have reached acceptable levels. The individuals' dosage may be adjusted accordingly.

EXAMPLE 4

Individual women are assessed and pre-screened to assemble an experimental group of subjects suffering from sexual dysfunction. The buccal drug dosage units of Examples 1 and 2 are each assessed in the experimental subjects for their ability to increase uterine or vaginal epithelial blood flow. Changes in blood flow or vaginal fluid production during and following buccal drug administration are determined using known methods. Increase in vaginal epithelial blood flow is determined using indirect methods such as photoplethysmography (Levin (1980) *Clinics in Obstet. Gynaecol.* 7: 213–252), heated oxygen electrode (Wagner et al. (1978), "Vaginal Fluid" in *The Human Vagina*, Evans et al. (eds.), Amsterdam: Elsevier/North Holland Biomedical Press, pp. 121–137), and direct clearance of radioactive Xenon (Wagner et al. (1980) *Obstet. Gynaecol.* 51:621–624). Changes in vulvar blood flow are monitored using laser Doppler velocimetry (Sarrel (1990) *Obstet. Gynaecol.* 75:26S–32S).

Decreased vaginal dryness and/or dyspareunia are negatively correlated with vaginal blood flow rates, wherein increased blood flow to the vagina correlates with increased lubrication and decreased frequency and severity of dyspareunia (Sarrel (1990) *Obstet. Gynaecol.* 75:26S–32S). Accordingly, vulvar blood flow after treatment is assessed using laser Doppler velocimetry and compared to baseline levels. Increased vaginal lubrication as a result of treatment with the vasodilating formulations can also be assessed using the methods of Semmens et al. (1982) *J. Am. Med Assoc.* 248:445–448. The buccal dosage units of the invention, including the units formulated as set forth in Examples 1 and 2, substantially increase blood flow to the vagina and vulvar area and alleviate vaginal dryness, as may be confirmed using the aforementioned methods.

What is claimed is:

1. A method for providing hormone replacement therapy to a female individual, comprising: (a) providing a buccal dosage unit comprised of a compressed tablet of a bioerodible polymeric carrier and therapeutically effective amounts of an androgenic agent; a progestin and an estrogen; and (b) affixing the dosage unit to the buccal mucosa of the individual and allowing the dosage unit to remain in place until erosion thereof is complete.

2. A method for providing hormone replacement therapy to a female individual, comprising: (a) providing a buccal dosage unit comprised of a compressed tablet of a bioerodible polymeric carrier and therapeutically effective amounts of a progestin and an estrogen; and (b) affixing the dosage unit to the buccal mucosa of the individual and allowing the dosage unit to remain in place until erosion thereof is complete.

3. The method of claim 1, wherein the androgenic agent is selected from the group consisting of androsterone, androsterone acetate, androsterone propionate, androsterone benzoate, androstenediol, androstenediol-3-acetate, androstenediol-17-acetate, androstenediol-3,17-diacetate, androstenediol-17-benzoate, androstenediol-3-acetate-17-benzoate, androstenedione, dehydro-epiandrosterone, sodium dehydroepiandrosterone sulfate, dromostanolone, dromostanolone propionate, ethylestrenol, fluoxymesterone, methyl testosterone, nandrolone phenpropionate, nandrolone decanoate, nandrolone furylpropionate, nandrolone cyclohexane-propionate, nandrolone benzoate, nandrolone cyclohexanecarboxylate, oxandrolone, oxymetholone, stanozolol, testosterone, 4-dihydrotestosterone, 5α-dihydrotestosterone, testolactone, pharmaceutically acceptable esters and salts thereof, and combinations of any of the foregoing.

4. The method of claim 3, wherein the androgenic agent is testosterone or a pharmaceutically acceptable ester thereof.

5. The method of claim 4, wherein the androgenic agent is a testosterone ester.

6. The method of claim 5, wherein the testosterone ester is selected from the group consisting of testosterone enanthate, propionate, cypionate, phenylacetate, acetate, buciclate, heptanoate, decanoate, undecanoate, caprate and isocaprate.

7. The method of claim 6, wherein the testosterone ester is selected from the group consisting of testosterone enanthate, propionate and cypionate.

8. The method of claim 4, wherein the androgenic agent is testosterone.

9. The method of claim 1, wherein the progestin is selected from the group consisting of acetoxypregnenolone, allylestrenol, anagestone acetate, chlormadinone acetate, cyproterone, cyproterone acetate, desogestrel, dihydrogesterone, dimethisterone, ethisterone, ethynodiol diacetate, flurogestone acetate, gestadene, hydroxyprogesterone, hydroxyprogesterone acetate, hydroxyprogesterone caproate, hydroxymethylprogesterone, hydroxymethyl-progesterone acetate, 3-ketodesogestrel, levonorgestrel, lynestrenol, medrogestone, medroxyprogesterone acetate, megestrol, megestrol acetate, melengestrol acetate, norethindrone, norethindrone acetate, norethisterone, norethisterone acetate, norethynodrel, norgestimate, norgestrel, norgestrienone, normethisterone, progesterone, and combinations thereof.

10. The method of claim 9, wherein the progestin is selected from the group consisting of progesterone, cyproterone acetate, norethindrone, norethindrone acetate and levonorgestrel.

11. The method of claim 10, wherein the progestin is progesterone.

12. The method of claim 1, wherein the estrogen is selected from the group consisting of 17α-estradiol, 17β-estradiol, ethynyl estradiol, pharmaceutically acceptable esters and ethers of 17α-estradiol, 17β-estradiol and ethynyl estradiol, estriol, estriol succinate, polyestrol phosphate, estrone, estrone acetate, estrone sulfate, piperazine estrone sulfate, quinestrol, mestranol and conjugated equine estrogens.

13. The method of claim 12, wherein the estrogen is 17β-estradiol or ethynyl estradiol.

14. The method of claim 1, wherein the androgenic agent is testosterone, the progestin is progesterone, and the estrogen is 17β-estradiol or ethynyl estradiol.

15. The method of claim 1, wherein the carrier is selected such that upon sustained contact with the buccal mucosa the unit completely erodes within a predetermined drug delivery period in the range of approximately 4 to 24 hours.

16. The method of claim 15, wherein the carrier is selected from the group consisting of carbomers, hydrolyzed polyvinylalcohol, polyethylene oxide, polyacrylates, hydroxypropyl methylcellulose, hydroxypropyl cellulose, and combinations thereof.

17. The method of claim 16, wherein the carrier is polyethylene oxide or a carbomer.

18. The method of claim 1, wherein the dosage unit has a total weight in the range of approximately 10 mg to 15 mg.

19. The method of claim 18, wherein the dosage unit has a total weight in the range of approximately 10 mg to 15 mg.

20. The method of claim 1, wherein the dosage unit comprises approximately 5 wt. % to 20 wt. % androgenic agent, 5 wt. % to 60 wt. % progestin, and 1 wt. % to 5 wt. % estrogen.

21. The method of claim 20, wherein the dosage unit comprises approximately 10 wt. % to 20 wt. % androgenic agent, 30 wt. % to 60 wt. % progestin, and 2 wt. % to 5 wt. % estrogen.

22. The method of claim 1, wherein the dosage unit comprises a tablet having a concave surface for contacting the buccal mucosa and adhering thereto.

23. The method of claim 1, wherein the dosage unit completely erodes within about 8 to about 24 hours after application to the buccal mucosa.

24. The method of claim 1, wherein the dosage unit is affixed to a region of the individual's upper gum between the first bicuspid on the left and the first bicuspid on the right.

25. The method of claim 2, wherein the progestin is selected from the group consisting of acetoxypregnenolone, allylestrenol, anagestone acetate, chlormadinone acetate, cyproterone, cyproterone acetate, desogestrel, dihydrogesterone, dimethisterone, ethisterone, ethynodiol diacetate, flurogestone acetate, gestadene, hydroxyprogesterone, hydroxyprogesterone acetate, hydroxyprogesterone caproate, hydroxymethylprogesterone, hydroxymethyl-progesterone acetate, 3-ketodesogestrel, levonorgestrel, lynestrenol, medrogestone, medroxyprogesterone acetate, megestrol, megestrol acetate, melengestrol acetate, norethindrone, norethindrone acetate, norethisterone, norethisterone acetate, norethynodrel, norgestimate, norgestrel, norgestrienone, normnethisterone, progesterone, and combinations thereof.

26. The method of claim 25, wherein the progestin is selected from the group consisting of progesterone, cyproterone acetate, norethindrone, norethindrone acetate and levonorgestrel.

27. The method of claim 26, wherein the progestin is progesterone.

28. The method of claim 2, wherein the estrogen is selected from the group consisting of 17α-estradiol, 17β-estradiol, ethynyl estradiol, pharmaceutically acceptable esters and ethers of 17α-estradiol, 17β-estradiol and ethynyl estradiol, estriba, estriol succinate, polyestrol phosphate, estrone, estrone acetate, estrone sulfate, piperazine estrone sulfate, quinestrol, mestranol and conjugated equine estrogens.

29. The method of claim 28, wherein the estrogen is 17β-estradiol or ethynyl estradiol.

30. The method of claim 2, wherein the progestin is progesterone and the estrogen is 17β-estradiol or ethynyl estradiol.

31. The method of claim 2, wherein the carrier is selected such that upon sustained contact with the buccal mucosa the unit completely erodes within a predetermined drug delivery period in the range of approximately 4 to 24 hours.

32. The method of claim 31, wherein the carrier is selected from the group consisting of carbomers, hydrolyzed polyvinylalcohol, polyethylene oxide, polyacrylates, hydroxypropyl methylcellulose, hydroxypropyl cellulose, and combinations thereof.

33. The method of claim 32, wherein the carrier is polyethylene oxide or a carbomer.

34. The method of claim 2, wherein the dosage unit has a total weight in the range of approximately 5 mg to 20 mg.

35. The method of claim 34, wherein the dosage unit has a total weight in the range of approximately 10 mg to 15 mg.

36. The method of claim 2, wherein the dosage unit comprises approximately 5 wt. % to 20 wt. % androgenic agent, 5 wt. % to 60 wt. % progestin, and 1 wt. % to 5 wt. % estrogen.

37. The method of claim 36, wherein the dosage unit comprises approximately 10 wt. % to 20 wt. % androgenic agent, 30 wt. % to 60 wt. % progestin, and 2 wt. % to 5 wt. % estrogen.

38. The method of claim 2, wherein the dosage unit comprises a tablet having a concave surface for contacting the buccal mucosa and adhering thereto.

39. The method of claim 2, wherein the dosage unit completely erodes within about 8 to about 24 hours after application to the buccal mucosa.

40. The method of claim 2, wherein the dosage unit is affixed to a region of the individual's upper gum between the first bicuspid on the left and the first bicuspid on the right.

* * * * *